United States Patent
Maeda et al.

(10) Patent No.: US 8,811,712 B2
(45) Date of Patent: Aug. 19, 2014

(54) DEFECT INSPECTION METHOD AND DEVICE THEREOF

(75) Inventors: Shunji Maeda, Yokohama (JP); Kaoru Sakai, Yokohama (JP); Hidetoshi Nishiyama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 248 days.

(21) Appl. No.: 13/141,375

(22) PCT Filed: Oct. 22, 2009

(86) PCT No.: PCT/JP2009/005561
§ 371 (c)(1),
(2), (4) Date: Jul. 26, 2011

(87) PCT Pub. No.: WO2010/073453
PCT Pub. Date: Jul. 1, 2010

(65) Prior Publication Data
US 2011/0274342 A1 Nov. 10, 2011

(30) Foreign Application Priority Data

Dec. 25, 2008 (JP) ................................ 2008-330894

(51) Int. Cl.
*G06K 9/00* (2006.01)
(52) U.S. Cl.
USPC ........................................................ 382/141
(58) Field of Classification Search
USPC ........................................................ 382/141
See application file for complete search history.

(56) References Cited

U.S. PATENT DOCUMENTS 7,630,535 B2 * 12/2009 Isomura ......................... 382/144
7,940,383 B2    5/2011 Noguchi et al.
(Continued)

FOREIGN PATENT DOCUMENTS

JP  10-089931  4/1998
JP  10-090192  4/1998
(Continued)

OTHER PUBLICATIONS

Takashi Hiroi et al., Precise Visual Inspection for LSI Wafer Patterns Using Subpixel Image Alignment, Proceedings o the Second IEEE workshop on Applications of Computer Vision Dec. 5-7, 1994.

(Continued)

*Primary Examiner* — Samir Ahmed
*Assistant Examiner* — Totam Le
(74) *Attorney, Agent, or Firm* — Antonelli, Terry, Stout & Kraus, LLP.

(57) ABSTRACT

The invention provides a defect inspection method and a defect inspection device which enable a defect to be inspected regardless of optical conditions. The invention comprises the steps of setting a target local region and a plurality of corresponding local regions in the image signals, the target local region including a target pixel and an area surrounding the target pixel, the corresponding local regions including pixels corresponding to the target pixel and areas surrounding the corresponding pixels; searching similarities between the image signal of the target local region and the image signals of the plurality of corresponding local regions; determining a plurality of image signals that represent corresponding local regions and are similar to the image signal of the target local region; and comparing the image signal of the target local region with the image signals that represent the corresponding local regions.

12 Claims, 12 Drawing Sheets

(56) References Cited

U.S. PATENT DOCUMENTS

| | | | |
|---|---|---|---|
| 8,055,057 B2* | 11/2011 | Kang et al. | 382/145 |
| 8,340,395 B2* | 12/2012 | Sakai et al. | 382/149 |
| 8,355,559 B2* | 1/2013 | Harada et al. | 382/141 |
| 2006/0067571 A1* | 3/2006 | Onishi | 382/149 |
| 2009/0196490 A1* | 8/2009 | Matsumiya | 382/149 |
| 2013/0148863 A1* | 6/2013 | Muraishi | 382/112 |

FOREIGN PATENT DOCUMENTS

| | | |
|---|---|---|
| JP | 10-340347 | 12/1998 |
| JP | 11-304718 | 11/1999 |
| JP | 2000-099727 | 4/2000 |
| JP | 2000-105203 | 4/2000 |
| JP | 2002-168799 | 6/2002 |
| JP | 2003-271927 | 9/2003 |
| JP | 2004-028836 | 1/2004 |
| JP | 2005-037166 | 2/2005 |
| JP | 2007-192688 | 8/2007 |
| JP | 2007-212201 | 8/2007 |
| JP | 2008-004863 | 1/2008 |
| JP | 2008-039533 | 2/2008 |

OTHER PUBLICATIONS

Kensuke Takeda, Interpolation-based Absolute Gradient Matching and Its Application for LSI Wafer Inspection, QCAV May 18-20, 2005.

Yasuyo Kita, Change Detection Using Joint Intensity Histogram, The Institute of Electronics, Information and Communication Engineers (IEICE) Transactions, 2007, pp. 1957-1965, vol. J90-D, No. 8.

Masamichi Sano, et al., One Class Classifier based on Proximity and Density Estimation, MIRU2008, IS3-6.

Akira Hamamatsu et al., Statistical Threshold Method for Semiconductor Inspection, $12^{th}$ a-PCNDT 2006,—Asia-Pacific Conference on NDT, Nov. 5-10, 2006, Auckland New Zealand.

Tetsuya Asami et al., A Saliency based abnormality detection algorithm for visual inspection, MIRU2008, IS5-2.

Shinji Maeda et al., Comparison Algorithm for LSI Wafer Multi-Layer Pattern Inspection Based on Scattergram Journal of Shingakukai, Jul. 2005, vol. J88-D-II No. 7.

Japanese Office Action; Application No. 2013-102708; mailing date: Jun. 3, 2014.

* cited by examiner

FIG. 1
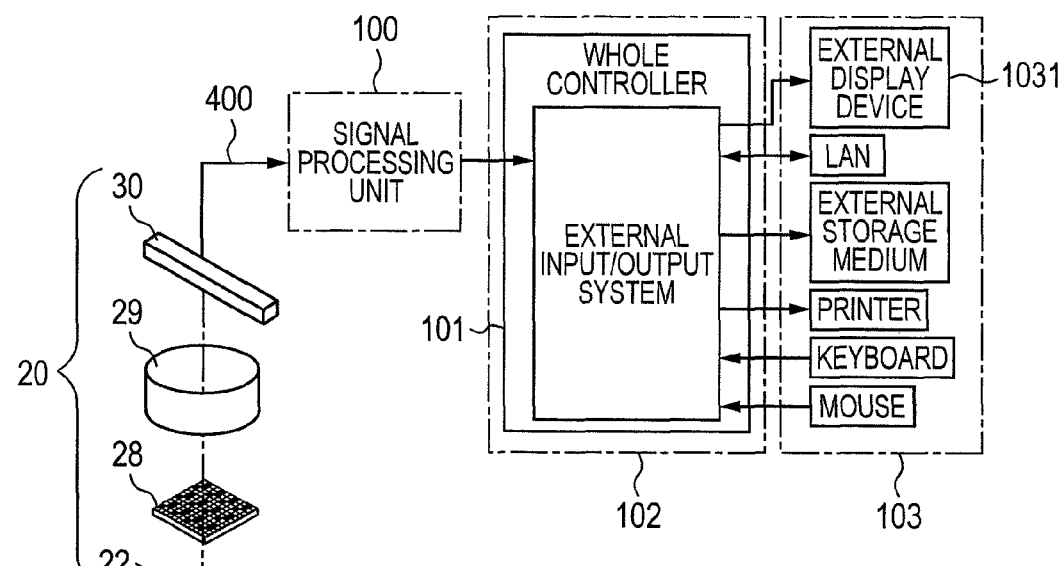
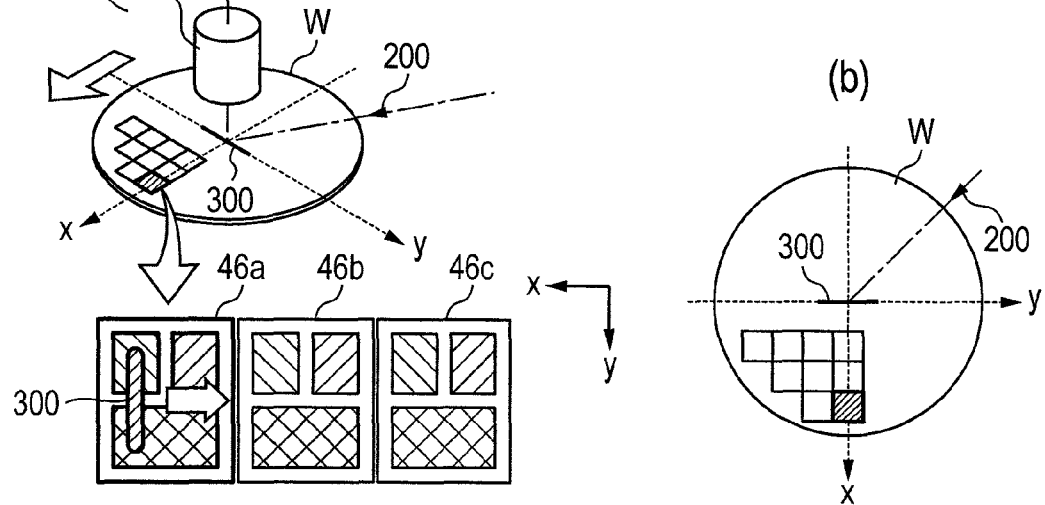

FIG. 4
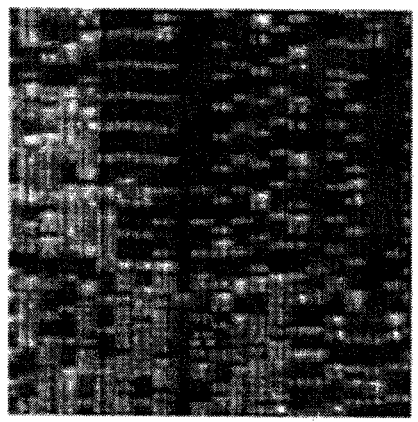
ORIGINAL IMAGE
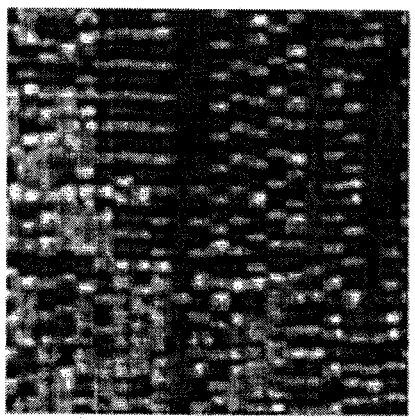
RESTORED IMAGE
Richardson-Lucy Deconvolution
(ONE OF IMAGE RESTORATION METHODS)

FIG. 5

(I) COMPARE THREE DIES
OPTICAL CONDITIONS
IMAGE MATCHING PERFORMED
BY AGM, NCC, ···

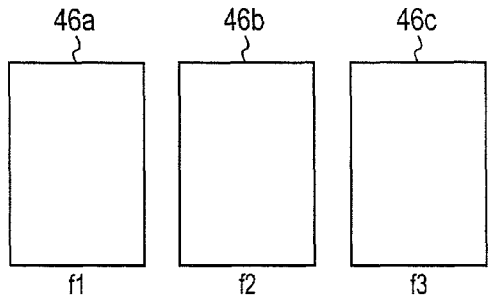

- MANY DIES ARE NOT USED
  (TO PREVENT VARIATION FROM BEING LARGE)
- SMALL NUMBER OF DATA PIECES USED FOR COMPARISON (II) SET CORRESPONDING LOCAL REGIONS
ON BOTH ADJACENT DIES
(SANDWICHING METHOD)
ASSUME THAT IT IS NORMAL

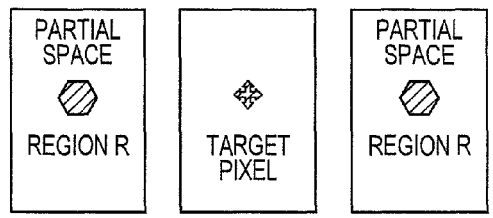

FIG. 6

(III) CATEGORIZE EACH OF PIXELS
IN CORRESPONDING
LOCAL REGIONS AND
FORM JOINT HISTOGRAM
FEATURE SPACE
(CATEGORIZATION IS
PERFORMED IN THE SAME
MANNER AS LIM)

USE JOINT HISTOGRAM
FEATURE SPACE
CATEGORIZE EACH OF PIXELS
AND FORM JOINT HISTOGRAM
FEATURE SPACE
WHEN PIXELS ARE FINELY
CATEGORIZED, CATEGORIZATION
CAUSES REDUCTION IN THE
AMOUNT OF DATA AND
ADVERSELY AFFECTS JOINT
HISTOGRAM FEATURE SPACE (IV) GENERATE THRESHOLD
FROM CONVEX HULL (ENVELOPE)

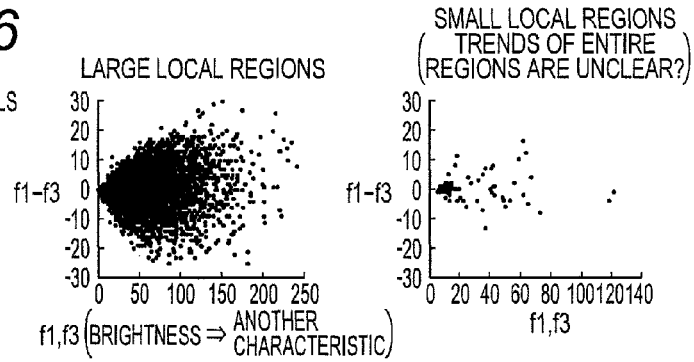

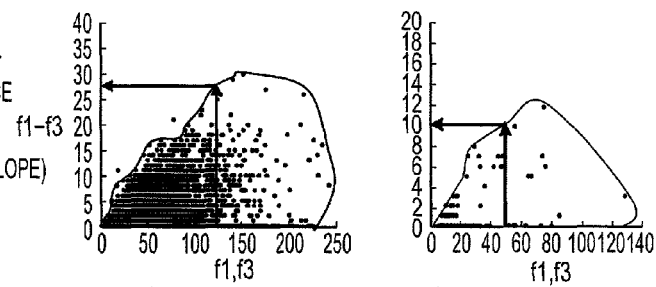

- VARIATION IS NOT CALCULATED, AND ENVELOPE (CONVEX HULL, R-CONCAVE HULL) IS CALCULATED
- LOCAL SUBSPACE METHOD IS USED FOR FEATURE SPACE (FOR EXAMPLE, centroid OF k-NEAREST NEIGHBORS)
- LOW-FREQUENCY POINTS (FOR EXAMPLE, FREQUENCY 1) MAY BE PIECEWISE CONTINUOUS

FIG. 7

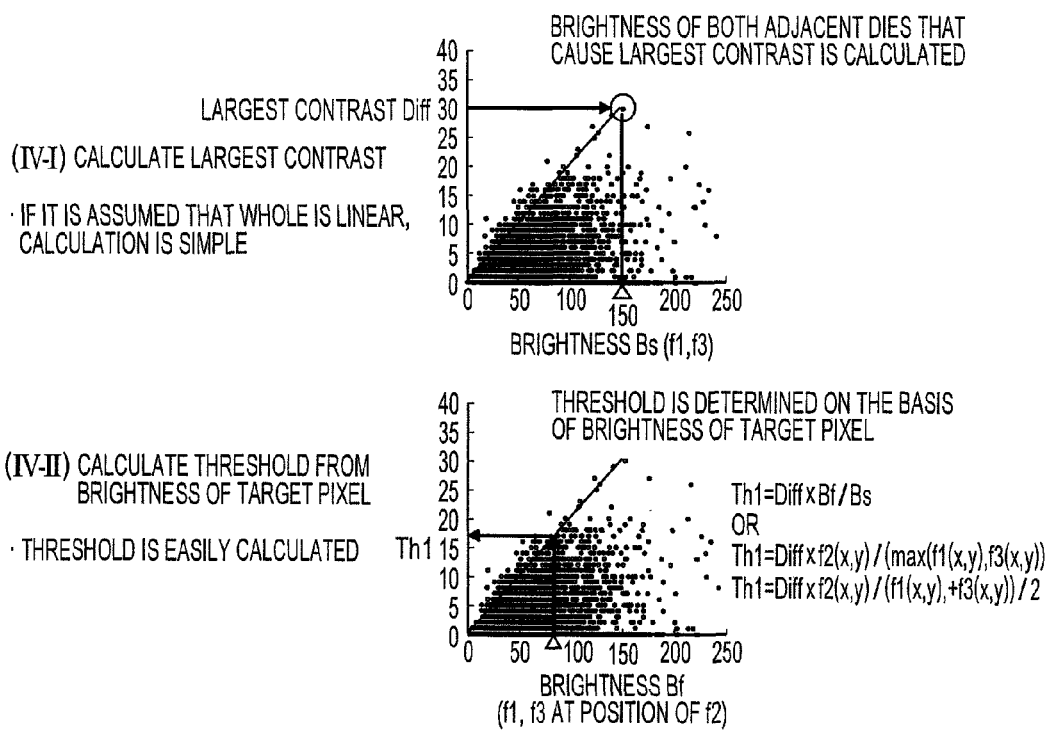

(IV-I) CALCULATE LARGEST CONTRAST
- IF IT IS ASSUMED THAT WHOLE IS LINEAR, CALCULATION IS SIMPLE (IV-II) CALCULATE THRESHOLD FROM BRIGHTNESS OF TARGET PIXEL
- THRESHOLD IS EASILY CALCULATED

FIG. 8

(V) CONSIDER POSITIONAL DISPLACEMENT
DETERMINE WEIGHT k ON THE BASIS OF ACCURACY OF IMAGE MATCHING (HALF-FIXED)

(VI) TRANSFER THRESHOLD TO SURROUNDING AREA (VII) CORRECT THRESHOLD FOR EDGE DIE ON THE BASIS OF EDGE FACTOR (MULTIPLICATION BY σ RATIO)

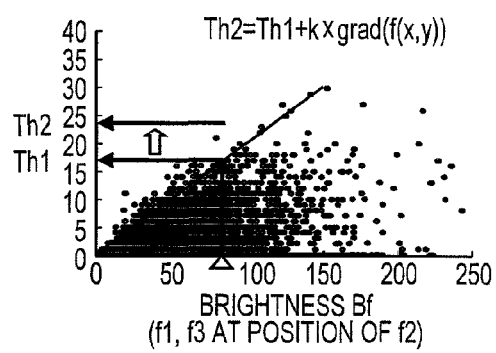

FIG. 11

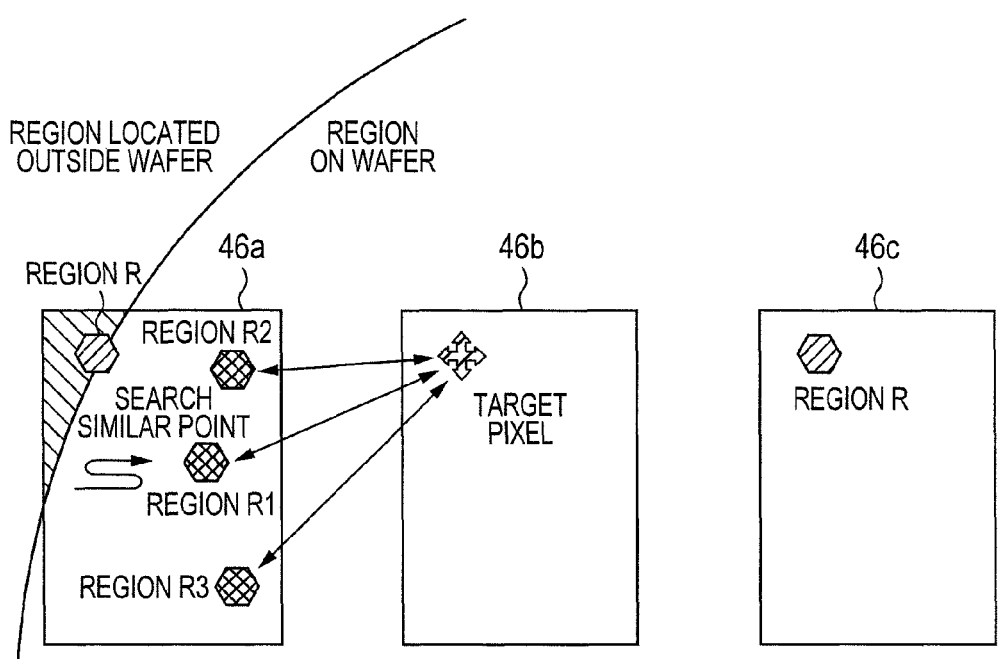

PROCESS PROCEDURES
- (S51) SEARCH SIMILAR CORRESPONDING LOCAL REGIONS ON ADJACENT DIES
- (S52) PERFORM REARRANGEMENT ON THE BASIS OF SIMILARITIES
- (S53) DETERMINE CORRESPONDING LOCAL REGIONS R1, R2, R3, ⋯ THAT ARE LOCATED ON ADJACENT DIES AND SIMILAR TO TARGET PIXEL (TARGET LOCAL REGION)
- (S54) COMPARE TARGET PIXEL (TARGET LOCAL REGION) WITH CORRESPONDING LOCAL REGIONS R1, R2, R3, ⋯
- (S55) DETERMINE DEFECT ACCORDING TO MAJORITY DECISION

US 8,811,712 B2

DEFECT INSPECTION METHOD AND DEVICE THEREOF

TECHNICAL FIELD

The present invention relates to a method and device for inspecting a defect that occurs during a process of manufacturing LSIs or FPD substrates for liquid crystal displays or plasma displays.

BACKGROUND ART

JP-A-2000-105203 (Patent Document 1) describes that a spatial filter blocks light refracted from a repeating pattern of a circuit pattern (that is a high-density repeating pattern and is not a repeating die and the like) located on a substrate to be inspected in order to inspect a foreign material or defect, which occurs during a process of manufacturing an LSI or a liquid crystal substrate. In addition, JP-A-2000-105203 describes that a technique for calculating a variation on the basis of a signal detected from a location at which the same circuit pattern is originally formed or a signal detected from a region located near the location, setting a judgment criterion (threshold) on the basis of the calculated variation, and extracting a signal indicating a defect such as a foreign material in a defect determination process.

In addition, JP-A-H10-90192 (Patent Document 2) describes a defect inspection method and a defect inspection device, which causes at least one of given inspection responses of a second pattern to be referenced in order to search a defect present at a point (to be inspected) located on a first pattern that has the same design as the second pattern and is located on a sample. JP-A-H10-90192 also describes the following technique. For the inspection, it is important to use points (to be observed) that correspond to each other and are located on the first and second patterns on the sample. The search is performed at least one time to generate at least two inspection responses. The two inspection responses (response signals from a dark field and a bright field are representative inspection responses) are separately detected by a photoelectric method and separately compared so that differential signals between the first and second patterns are individually formed. Specifically, first and second responses are detected from the first pattern. The detection results are compared with two responses detected from corresponding points (to be inspected) of the second pattern. As a result, the first and second differential signals of the responses are formed.

The individually formed differential signals are subjected to data processing in order to determine a unified list of defects of the first pattern. Specifically, the first and second differential signals are collectively subjected to data processing, and the unified list of defects of the first pattern can be determined. After that, the first pattern defect list may be subjected to data processing. Then, a known, neglectable and false defect that can be viewed on the sample surface is extracted and removed. The known, neglectable and false defect is provided to a user as a reference. In addition, a various types of search for inspection are performed to increase inspection responses, and two or more optical responses are obtained from the sample and processed. Thus, the inspection accuracy is further improved. In addition, a photoelectric detector is arranged on the back side of a transparent sample, and inspection responses are collected using transmitted light. Thus, the accuracy of the aforementioned pattern defect list can be improved. In addition, a defect that is concealed in the sample can be searched.

RELATED ART LITERATURE

Patent Document

Patent Document 1: JP-A-2000-105203
Patent Document 2: JP-A-H10-90192

Non-Patent Document

Non-Patent Document 1: T. Hiroi, S. Maeda, H. Kubota, K. Watanabe, Y. Nakagawa "Precise Visual Inspection for LSI Wafer Patterns Using Subpixel Image Alignment", Proc. of 2nd IEEE workshop on Applications of Computer Vision (1994)
Non-Patent Document 2: K. Takeda, S. Kaneko, T. Tanaka, K. Sakai, S. Maeda, Y. Nakagawa "Interpolation-based Absolute Gradient Matching and Its Application for LSI Wafer Inspection", QCAV 2005, May 18-20 (2005)
Non-Patent Document 3: Yasuyo Kita "Change Detection Using Joint Intensity Histogram" The Institute of Electronics, Information and Communication Engineers (IEICE) Transactions Vol. J90-D, No. 8, pp. 1957-1965
Non-Patent Document 4: Masamichi Sano, Takekazu Kato, Toshikazu Wada, Kaoru Sakai, Shunji Maeda "One Class Classifier based on Proximity and Density estimation", MIRU2008, IS3-6 (2008)
Non-Patent Document 5: Akira Hamamatsu, Hisae Shibuya, Hidetoshi Nishiyama, Yoshimasa Oshima, Shunji Maeda, Minoru Nogushi "STATISTICAL THRESHOLD METHOD FOR SEMICONDUCTOR INSPECTION" View 2004 (2004)
Non-Patent Document 6: Tetsuya Asami, Takekazu Kato, Toshikazu Wada, Kaoru Sakai, Shunji Maeda "A saliency based abnormality detection algorithm for visual inspection" MIRU2008, IS5-2 (2008)
Non-Patent Document 7: Shunji Maeda, Kaoru Sakai, Takashi Okabe: "Comparison Algorithm for LSI Wafer Multi-Layer Pattern Inspection Based on Scattergram Information", Journal of Shingakukai, J88-D-11, 7 (2005) 1173

SUMMARY OF THE INVENTION

Problems to be Solved by the Invention

Patterns formed on an object (for example, semiconductor wafer) to be processed in manufacturing of an LSI or an FPD substrate include a repeating pattern (high-density repetition) represented by a dynamic random access memory (DRAM) or a random pattern (non-repeating pattern) represented by a logic. A die is obtained by cutting the object and is a unit that forms a single memory element or a processor element. The die is formed on a wafer substrate. When a foreign material is attached to the surface of the object to be processed or a defect occurs on the surface of the object to be processed in the process of manufacturing the LSI or the flat panel display (FPD) substrate, the foreign material or the defect may cause an insulation failure of a wiring or a short circuit, for example. With the microfabrication of circuit patterns, it is difficult to distinguish a pattern (non-defective portion) formed on the object to be processed from a fine foreign material or a fine defect. For example, when optical conditions (the wavelength of illumination, polarization of the illumination, an azimuth of the illumination, an elevation of the illumination, a numerical aperture for an illumination beam, an azimuth of light to be detected, an elevation of the light to be detected, polarization of the light to be detected, a numerical aperture for the light to be detected and the like) that enable a foreign material or any of various defects to be detected vary depending on the defect, it is necessary to change the optical conditions for each of the defects. In addition, it is difficult to distinguish the non-defective portion from a defect under a single group of optical conditions. In this case, it is necessary to inspect a single type of defects under multiple groups of optical conditions. Thus, an inspection speed (throughput) may be reduced.

The difference between normal portions may be relatively larger than defects due to roughness of a pattern or a variation in the thicknesses. Even when appropriate optical conditions are selected, it is difficult to set a threshold for determination of a defect. Especially, it is necessary to set a threshold for each of groups of optical conditions, and it takes time to create an inspection recipe.

It is an object of the present invention to provide a defect inspection method and a defect inspection device which enable a defect to be inspected while distinguishing regardless of optical conditions, between a defectless circuit pattern and the defect (or a foreign material) that occurs on at least one of various patterns formed on an object to be processed in a process of manufacturing an LSI or an FPD substrate. Partial inspection needs to be performed on patterns (instead of the entire surface of a wafer) in an inspection of a semiconductor circuit pattern due to a reduction (caused by an increase in sensitivity and causing a reduction in throughput) in the size of a pixel to be detected, or due to an increase in the diameter of the wafer to φ 300 mm to φ 450 mm, or for a limited inspection of a problem portion represented by a hot spot in which a margin for exposure or etching is insufficient. However, conventional methods do not support the partial inspection.

Another object of the present invention is to provide a defect inspection method and a defect inspection device which enables a stable inspection to be performed even when a number of optical conditions is provided and the number of image signals to be compared is small.

Means for Solving the Problems

In order to accomplish the objects, according to the present invention, for example, a method and device for acquiring image signals from a substrate that is to be inspected, the substrate having circuit patterns repeatedly formed in dies, and inspecting a defect present on the substrate on the basis of the acquired image signals includes the steps of: setting a target local region and a plurality of corresponding local regions in the acquired image signals, the target local region including a target pixel and an area surrounding the target pixel, the corresponding local regions including pixels corresponding to the target pixel and areas surrounding the corresponding pixels; forming a joint histogram feature space of the corresponding local regions on the basis of the image signals of the corresponding local regions set in the local region setting step; determining a threshold on the basis of the joint histogram feature space formed in the forming step; and detecting the defect present on the target local region on the basis of differential images between the target local region and the corresponding local regions using the threshold determined in the threshold determining step.

In addition, according to the present invention, it is preferable that in the forming step, pixels be categorized on the basis of feature amounts of the pixels and a joint histogram feature space be formed for each of categories in the forming step.

In addition, according to the present invention, it is preferable that in the forming step, the joint histogram feature space of the corresponding local regions be formed with axes that indicate brightness and a difference, which are calculated from the image signals of the corresponding local regions.

In addition, according to the present invention, it is preferable that in the threshold determining step, a convex hull be calculated from the joint histogram feature space of the corresponding local regions and the threshold be determined on the basis of the convex hull, the joint histogram feature space being formed in the forming step.

In addition, according to the present invention, it is preferable that in the threshold determining step, the maximum value (Diff) of differences, and brightness (Bs) corresponding to the maximum value of the differences, be calculated from the joint histogram feature space of the corresponding local regions, and the threshold be determined using the calculated maximum value (Diff) of the differences and the brightness corresponding to the maximum value (Diff) on the basis of brightness (Bf) obtained from the image signal of the target local region set in the local region setting step, the joint histogram feature space being formed in the forming step.

In addition, according to the present invention, it is preferable that a value be added to the threshold on the basis of the accuracy of image matching in the threshold determining step.

In addition, according to the present invention, it is preferable that the defect inspection method further include an image improving step of using a point spread function indicating a degradation of an optical system to restore degradations of the image signals acquired from the substrate to be inspected before the local region setting step.

In addition, according to the present invention, a defect inspection method for acquiring image signals from a substrate that is to be inspected, the substrate having circuit patterns repeatedly formed, and inspecting a defect present on the substrate on the basis of the acquired image signals includes the steps of: setting a target local region and a plurality of corresponding local regions in the acquired image signals, the target local region including a target pixel and an area surrounding the target pixel, the corresponding local regions including pixels corresponding to the target pixel and areas surrounding the corresponding pixels; searching similarities between the image signal of the target local region set in the local region setting step and the image signals of the plurality of corresponding local regions set in the local region setting step; determining, using information of the similarities searched in the searching step, a plurality of image signals that represent corresponding local regions and are similar to the image signal of the target local region; and comparing the image signal of the target local region with the image signals that represent the corresponding local regions and have been determined in the determining step to comprehensively determine the defect.

In addition, according to the present invention, it is preferable that the defect inspection method further include the steps of: forming a joint histogram feature space of the corresponding local regions on the basis of the image signals of the corresponding local regions set in the local region setting step; determining a threshold on the basis of the joint histogram feature space formed in the forming step; and using the threshold determined in the threshold determining step to detect the defect present on the target local region on the basis of differential images between the target local region and the corresponding local regions.

Effects of the Invention

According to the present invention, it is possible to detect a fine defect on a semiconductor wafer (tending to be more precise and have a larger diameter) or an FPD substrate (tending to be more precise and have a larger diameter) with high sensitivity without an effect of roughness of a pattern and a variation in thicknesses. Especially, it is possible to detect a defect while distinguishing between a defectless circuit pattern and the defect regardless of various optical conditions. In addition, it is possible to inspect the defect using a small number of dies and a small amount of data. Furthermore, it is possible to perform a limited inspection of a problem portion represented by a hot spot in a die.

It is considered that the shape of a pattern of a die that is located far from a target die is different from the shape of a pattern of the target die. Thus, according to the present invention, dies to be compared are limited to dies located near the target die so that unnecessary information is removed; many dies located near the target die are specified to compare the target die with the dies; it is possible to extract a defect with high sensitivity by comprehensively determining the defect on the basis of a region that is located near a target region and has a similar feature; and it is possible to inspect a systematic defect.

BRIEF DESCRIPTION OF THE DRAWINGS

FIG. 1(a) is a schematic diagram illustrating an embodiment of a defect inspection device according to the present invention, and FIG. 1(b) is a plan view of a semiconductor wafer.

FIG. 4 is a diagram illustrating an example (method called Richardson-Lucy) of an image quality improvement made in the first embodiment of the signal processing unit included in the defect inspection device according to the present invention.

FIG. 5 is a diagram illustrating (I) matching of images that are acquired under predetermined optical conditions and represent three dies to be compared, and (II) setting of corresponding local regions R on dies adjacent to a target die that has a target pixel, in the first embodiment of the signal processing unit included in the defect inspection device according to the present invention.

FIG. 6 is a diagram illustrating (III) formation of a joint histogram feature space on the basis of the corresponding local regions and (IV) first procedures of determining a threshold on the basis of the joint histogram feature space formed on the basis of the corresponding local regions, in the first embodiment of the signal processing unit included in the defect inspection device according to the present invention.

FIG. 7 is a diagram illustrating (IV-I) and (IV-II) simple versions of the first procedures of determining a threshold on the basis of the joint histogram feature space formed on the basis of the corresponding local regions, in the first embodiment of the signal processing unit included in the defect inspection device according to the present invention.

FIG. 8 is a diagram illustrating (V), (VI) and (VII) second procedures of determining a threshold on the basis of the joint histogram feature space formed on the basis of the corresponding local regions, in the first embodiment of the signal processing unit included in the defect inspection device according to the present invention.

FIG. 11 is a diagram illustrating second process procedures of a within-die comparison method to be performed in the second embodiment of the signal processing unit included in the defect inspection device according to the present invention.

MODE FOR CARRYING OUT THE INVENTION

Figure 2:
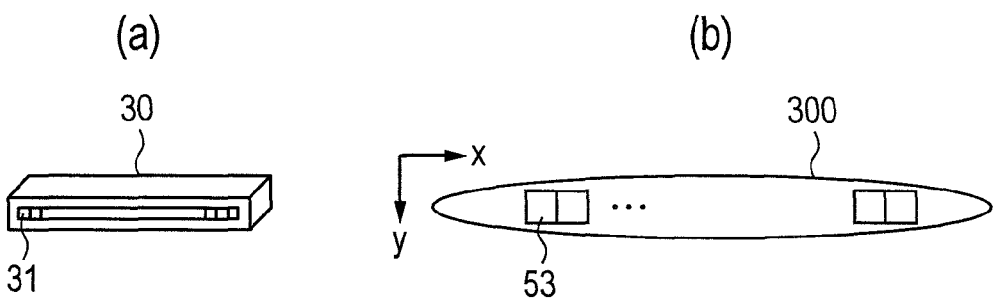
FIG. 2(a) is a diagram illustrating a linear sensor included in the defect inspection device according to the present invention.
FIG. 2(b) is a diagram illustrating an illuminated area located on a substrate to be inspected, and pixels projected on the substrate to be inspected.

Embodiments of a defect inspection method according to the present invention and a defect inspection device according to the present invention will be described with reference to the accompanying drawings.

For the simplification of description, the same constituent elements are indicated by the same reference numerals.

First Embodiment

FIG. 1(a) is a diagram illustrating a schematic configuration of a dark-field defect inspection device that is an embodiment of the defect inspection device according to the present invention. FIG. 1(b) is a plan view of a semiconductor wafer. The dark-field defect inspection device includes a dark-field illumination optical system (not illustrated) and a detection optical system 20. The dark-field illumination optical system performs dark-field illumination to illuminate the surface of the semiconductor wafer (substrate to be inspected) W in a predetermined azimuth from a direction inclined at a certain angle (hereinafter referred to as an elevation) with respect to the normal to the surface of the semiconductor wafer W. The dark-field illumination optical system may emit P-polarized illumination light or S-polarized illumination light. The detection optical system 20 includes an objective lens 22, a spatial filter 28, an imaging lens 29 and a linear sensor 30. The objective lens 22 collects light (including scattered light and refracted light) reflected from the semiconductor wafer (substrate to be inspected) W. The spatial filter 28 is arranged on a Fourier transform plane. The imaging lens 29 images the reflected light (including the scattered light and the refracted light) that has passed through the spatial filter 28. The linear sensor 30 receives the light imaged by the imaging lens 29 and performs photoelectric conversion on the light. The detection optical system 20 may include an analyzer that is controlled to rotate around an optical axis so that the linear sensor 30 can detect a specific polarized light component.

The surface (of the semiconductor wafer W) to be scanned in X direction is subjected to dark-field illumination and thereby illuminated with illumination light 200 from a predetermined azimuth-elevation direction that is inclined at an angle with respect to the normal to the surface of the semiconductor wafer W so that a spot of a linear beam 300 is formed on the semiconductor wafer W and a longitudinal direction of the linear beam 300 is parallel to Y direction. The linear beam 300 causes light to be scattered and refracted from a foreign material, a defect or a pattern on the semiconductor wafer W. Then, the scattered and refracted light is collected by the objective lens 22 from a direction (or vertical direction) parallel to the normal to the semiconductor wafer W, for example. When the pattern that is formed on the semiconductor wafer W has high-density repeating portions, light that is refracted from the repeating pattern (cyclic circuit pattern) is collected by an exit pupil of the objective lens 22 or regularly collected on the Fourier transform plane as a refracted image. Thus, the light is blocked by the spatial filter 28 that is arranged on the Fourier transform plane. Light that is refracted and scattered from a foreign material, a defect and a pattern (excluding the repeating pattern) on the semiconductor wafer W passes through the spatial filter 28, and is guided to the imaging lens 29 and imaged on the linear sensor 30, for example.

FIG. 2(a) is a perspective view of an example of the linear sensor that performs imaging. FIG. 2(b) is a diagram illustrating pixels of the linear sensor that performs imaging. As illustrated in FIG. 2(a), pixels 31 of the linear sensor 30 are one-dimensionally arranged. As illustrated in FIG. 2(b), when detection magnification is set so that sensor pixels 53 are projected in the spot of the linear beam 300 on the semiconductor wafer W, light that is refracted and scattered from the linear region can be collectively detected. The semiconductor wafer W is placed on an X-Y stage (not illustrated) and scanned in X and Y directions so that a two-dimensional image of the semiconductor wafer W is obtained. In this case, a main scanning direction is set to a direction perpendicular to the longitudinal direction of the linear beam 300, or X direction, and the semiconductor wafer W is moved in a stepwise manner in Y direction a distance corresponding to the length of the sensor pixels 53 (projected on the semiconductor wafer W) per step so that the whole surface of the semiconductor wafer W can be inspected at a high speed. The refracted and scattered light received by the linear sensor 30 is subjected to the photoelectric conversion and transmitted as an image signal 400 to a signal processing unit 100 that performs signal processing and is a feature of the present invention.

Figure 3:
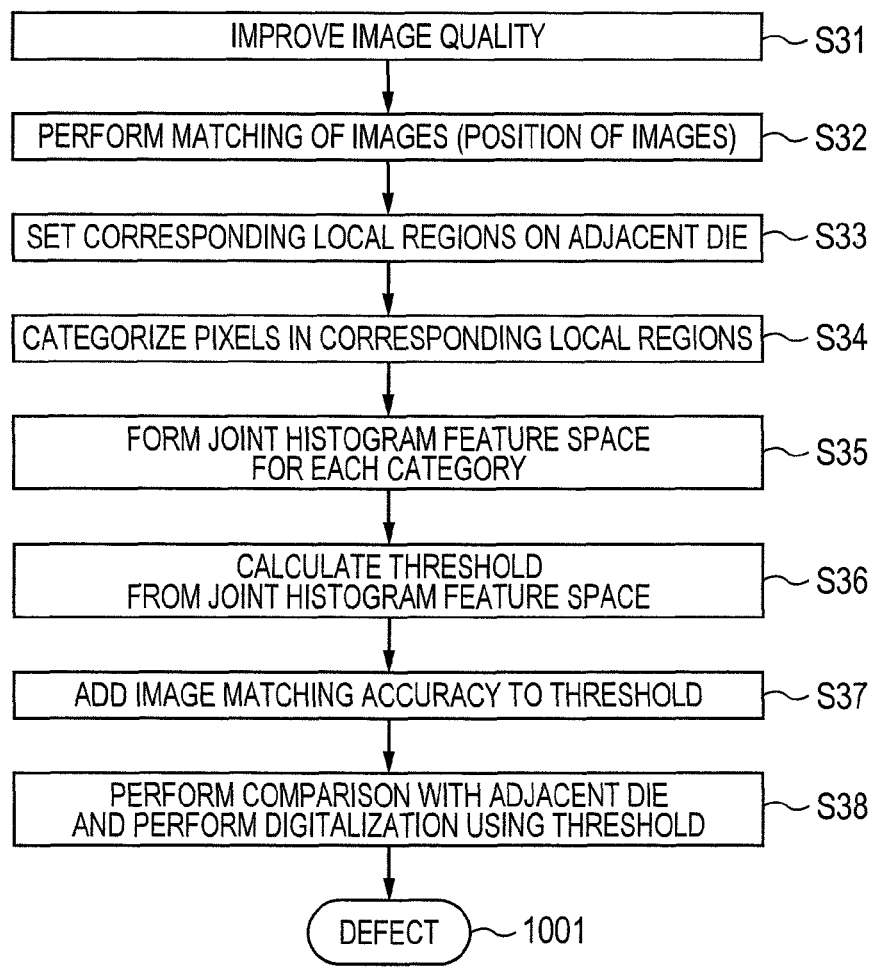
FIG. 3 is a flowchart of procedures of a process to be performed in a first embodiment of a signal processing unit included in the defect inspection device according to the present invention.

Next, a first embodiment of the signal processing unit 100 that is the feature of the present invention is described below. In the first embodiment, the signal processing unit 100 is constituted by a computer provided with a memory (storage device). The signal processing unit 100 compares a first image signal acquired from a target die with another die (repeating circuit pattern) adjacent to the target die and performs an inspection. Specifically, as illustrated in FIG. 3, the signal processing unit 100 improves the quality of an image of the received image signal 400 in accordance with a program by (1) restoring a degradation of the optical system, and the image signal is stored in the image memory (not illustrated) (S31). Next, the signal processing unit 100 performs matching of an image (acquired from the image memory) of the target die with an image (acquired from the image memory) of the adjacent die (S32). Then, (2) a target local region that includes a target pixel on the target die and an area surrounding the target pixel is set, and corresponding local regions R that include pixels (each of which is located on the adjacent die or the target die and corresponds to the target pixel) and areas surrounding the pixels are set (S33). Then, (3 to 5) the pixels that are included in the set corresponding local regions R are grouped (categorized on a pixel basis) on the basis of feature amounts of the pixels (S34). A joint histogram feature space is formed for each category (S35). A threshold (Th1) is calculated from the formed joint histogram feature space (S36). (6) A value is added to the threshold on the basis of the accuracy of the image matching are summed (S37). An image signal of the target local region of the target die is compared with image signals of the plurality of corresponding local regions, each of which is located on the adjacent die or the target die, and the signals are binarized using the threshold (Th1). Then, a defect 1001 is detected (S38).

The signal processing unit 100 is connected to a whole controller 101. The whole controller 101 has an external input/output system 102 so that a parameter or the like can be set and changed from the external. The whole controller 101 is connected to external devices 103 such as a mouse, a keyboard, a printer and the like. Thus, a part of signal processing to be performed by the signal processing unit may be performed by the whole controller 101.

Next, the signal processing (to be performed by the signal processing unit 100) according to the embodiment of the present invention is described with reference to FIGS. 4 to 8. The image signals that are obtained in the embodiment illustrated in FIG. 1 are described.

The image quality improvement (S31) is first performed to correct (improve) the qualities of images of the acquired image signals. An example of the processing is illustrated in FIG. 4. A point spread function that represents a degradation of the optical system is used to restore degradations of the images. Methods used for the restoration include a Richardson-Lucy method using Bayes' theorem, an iterative back projection (IBP) method, a total variation method (BTV) using a bilateral filter, and the like. FIG. 4 illustrates the results obtained using the Richardson-Lucy method. When a defect is determined using this restored image, the intensity of a signal obtained from the defect (shining in a dot shape on a dark-field image) is increased and an effect of removing noise is obtained. Thus, it has been confirmed that sensitivity of defect detection is improved.

As illustrated in FIG. 5, as targets that are obtained under predetermined optical conditions and are to be compared, a target die (46b) and dies (or dies (46a, 46c) located adjacent to the target dies on the right and left sides of the target die (46b)) located in the vicinity of the target die (46b) are used. In this case, dies that are located adjacent to the target die on the upper and lower sides of the target die may be used. In this example, the three dies (46a, 46b, 46c) are compared, while the three dies are the target die and the dies located adjacent to the target die on the right and left sides of the target dies. Image signals of the three dies are indicated by f1(x, y), f2(x, y) and f3(x, y) and illustrated from the left side of FIG. 5. In step S32, image matching is performed on images of the image signals by absolute gradient matching (AGM), normal cross correlation (NCC) or the like to position the image signals. In the image matching, a method that is described in Non-Patent Document 1 "T. Hiroi, S. Maeda, H. Kubota, K. Watanabe, Y. Nakagawa "Precise Visual Inspection for LSI Wafer Patterns Using Subpixel Image Alignment", Proc. Of 2nd IEEE workshop on Applications of Computer Vision (1994)" can be used to position the image signals with subpixel accuracy, for example. In addition, a method that is described in Non-Patent Document 2 "K. Takeda, S. Kaneko, T. Tanaka, K. Sakai, S. Maeda, Y. Nakagawa "Interpolation-based Absolute Gradient Matching and Its Application for LSI Wafer Inspection", QCAV 2005, May 18-20 (2005)" can be used.

Next, in step S33, corresponding local regions R that are located in the vicinity of pixels corresponding to the target pixel and surround the corresponding pixels are set in the image signals f1 and f3 of the adjacent dies in consideration that a defect of a target local region that surrounds the target pixel and is located in the vicinity of the target pixel is determined, as illustrated in item (II) of FIG. 5, for example. The corresponding local regions R include the pixels corresponding to the target pixel in the image signal f2 of the target die and are set so that the corresponding local regions R surround and are located in the vicinity of the corresponding pixels in the image signals f1 and f3 of the dies adjacent to the target die, for example. The sizes of the corresponding local regions R depend on a technology node of the target pattern, the optical magnification and the sizes of the pixels to be detected. The sizes of the corresponding local regions R can be set to 7×7 pixels, 13×13 pixels, 33×33 pixels or the like.

Attention is directed to the fact that target data is limited and a large amount of data is not included. When a large amount of data is included, there is an advantage that a variation in the dies can be reflected. However, excessive information other than the dies to be compared may be included. Thus, in order to minimize the data, the dies to be compared are limited to the dies (for example, adjacent dies) located in the vicinity of the target die. In addition, regions in the dies are set as the corresponding local regions R. For example, the dies that are adjacent to the target die are set so that the adjacent dies sandwich the target die. The plurality of corresponding local regions R may be located on the target die so that the corresponding local regions R sandwich the target local region. It is assumed that the aforementioned corresponding local regions R do not include a defect (the assumption is correct with a high probability). Even if the corresponding local regions R each include a defect, an adverse effect does not substantially occur.

Next, in steps 34 and 35, the pixels that are located in the corresponding local regions are categorized in the same manner as a method described in Non-Patent Document 7 "LIM (Shunji Maeda, Kaoru Sakai, Takashi Okabe: Comparison Algorithm for LSI Wafer Multi-Layer Pattern Inspection Based on Scattergram Information, Journal of Shingakukai, J88-D-11, 7 (2005)1173.", and a joint histogram feature space is formed as shown in FIG. 6(III). The joint histogram feature space is a scattergram. For example, the joint histogram feature space of the local regions is a data scattergram that is formed using, as the axes of the scattergram, the difference between the image signals f1(x, y) and f3(x, y) of the corresponding local regions and brightness (gray-scale f1, f3) of the image signals f1(x, y) and f3(x, y), for example. In FIG. 6, a difference (f1−f3) and an absolute value of the difference (f1−f3) are indicated as the differences, while the sizes of the local regions are changed. The intervals of the axis may not be set on a gray-scale basis and may be set to a certain unit. It is apparent that when the sizes of the corresponding local regions R are extremely small, the trends of the data cannot be recognized. It is preferable that the sizes of the corresponding local regions be set so that a boundary of the data is relatively clear. The joint histogram feature space indicates a two-dimensional density histogram in many cases. However, the joint histogram feature space may be a two- or more-dimensional histogram.

In addition, when the joint histogram feature space is normalized using a total frequency, the joint histogram feature space can be treated as a probability density function. When the joint histogram feature space is considered as the probability density function, a concept such as an entropy, the amount of mutual information, a Kullback-Leibler information amount or a Kullback-Leibler divergence can be used.

In general, the magnitude of a variation in a probability density distribution can be evaluated using an information amount (entropy) of the distribution. When the variation is uniformly distributed, the entropy is largest. When the variation is concentrated at a certain position in the distribution, the entropy is smallest. When two images are indicated by A and B, an information amount H(A, B) (joint entropy) that is calculated from a joint histogram of the images is the maximum value H(A)+H(B) when the two images are not correlated with each other. As the correlation between the images is higher, the information amount H(A, B) is smaller.

The Kullback-Leibler divergence is a measure of the difference between two probability distributions (actual probability distribution P and arbitrary probability distribution Q) given by a probability theory and an information theory. The Kullback-Leibler divergence is called an information divergence, an information gain, or a relative entropy.

It is preferable that the joint histogram feature space of the corresponding local regions R be each formed by grouping pixels on the basis of feature amounts of the pixels and organizing pixels having similar features for each group of pixels having similar features. As the feature amounts, existing values such as brightness, differential values or standard deviations can be used.

When a joint histogram feature space with an axis of brightness (of the corresponding pixels) calculated from the image signals of the cut corresponding local regions R is formed and treated as a probability density function, and mutual information amounts are calculated as numbers, similarities of the image signals of the corresponding local regions can be determined. The difference between the positions of the image signals can be evaluated. The joint histogram feature space represents existence probabilities of the corresponding pixels in the image signals. The distribution varies due to a change in the image signals. When the image signals are changed so that the distribution is small, registration of the image signals can be performed. In the aforementioned image matching method, the accuracy can be evaluated using the mutual information amounts or the like.

The joint histogram is described in Non-Patent Document 3 "Yasuyo Kita "Change Detection Using Joint Intensity Histogram" The Institute of Electronics, Information and Communication Engineers (IEICE) Transactions Vol. J90-D, No. 8, pp. 1957-1965", or the like.

Next, in step S36, as illustrated in item (IV) of FIG. 6, the relationship between the brightness (f1, f3) and the difference (|f1−F3|) is represented using a convex hull (envelope) in the joint histogram feature space. The difference (|f1−F3|) that corresponds to the brightness (f1, f3) is used as the threshold (Th1) to determine a defect in the target local region.

Attention is directed to an active calculation of a boundary without a calculation of a variation in data. Thus, the boundary is calculated by:

calculating an envelope (convex hull, R-concave hull);

using a local subspace method for the feature space (for example, the centroid of k-nearest neighbors);

causing low-frequency points (for example, frequency 1) to be piecewise continuous; or the like.

The boundary may be calculated using a generation type classifier. In addition, the boundary may be calculated using an identification type classifier.

The convex hull forms a convex polygon that includes all points of a point group and all vertexes of the polygon and has the smallest area. As a calculation of the convex hull, a wrapping method, Graham's scan algorithm, an incremental method, a division and conquer algorithm and the like are known. The R-concave hull is based on a convex hull and formed by a method described in Non-Patent Document 4 "Masamichi Sano, Takekazu Kato, Toshikazu Wada, Kaoru Sakai, Shunji Maeda "One Class Classifier based on Proximity and Density estimation", MIRU2008, IS3-6 (2008)".

The centroid of the k-nearest neighbors is the centroid of k data pieces located near data pieces between which the difference is largest. The centroid of the k data pieces is treated as a threshold. If it cannot be assumed that the pixels in the corresponding local regions are normal, this method is effective. A parameter k is set to 3, for example. Similarly to the R-concave hull, a margin can be added to the threshold on the basis of the density of the data pieces located near the data pieces between which the difference is largest.

When the comparison method is based on the difference between dies, the difference calculated from the image signals and the brightness calculated from the image signals are appropriate to be plotted along the axes of the joint histogram feature space. When the comparison method is not based on the difference between the dies and is based on the difference between differential values, the differential values and the difference calculated by differentiating the image signals are appropriate to be plotted along the axes of the joint histogram feature space of the corresponding local regions. The axes of the joint histogram feature space are determined on the basis of targets to be compared for detection of a defect.

In the aforementioned method, the threshold (Th1) to determine a defect in the target local region is calculated.

Next, a simple method for calculating the threshold is described with reference to items (IV-I) and (IV-II) of FIG. 7. Specifically, it is assumed that the joint histogram feature space of the corresponding local regions R has a linear property, and the maximum (maximum contrast) (Diff) of an absolute value of the difference is calculated. Next, the threshold Th1 is set using the following Equation (1) or (2).

$$Th1 = Diff \times Bf/Bs \quad (1)$$

In Equation (1), Bf is the brightness of the adjacent dies (f1, f3) that cause the maximum contrast Diff, while Bs is the brightness of the target pixel (position of f2).

$$Th1 = Diff \times f2(x,y)/(\max(f1(x,y), f3(x,y)))$$

$$Th1 = Diff \times f2(x,y)/(f1(x,y) + f3(x,y))/2 \quad (2)$$

When boundary data has a linear property in the joint histogram feature space formed by the brightness calculated from the image signals and the difference calculated from the image signals, the calculation is simple.

Next, in step S37, as illustrated in item (V) of FIG. 8, a threshold Th2 is expressed by the following Equation (3) using the calculated threshold Th1 in consideration of remaining positional displacement (in consideration of the accuracy of the image matching).

$$Th2 = Th1 + k2 \times \text{grad}(f2(x,y)) \quad (3)$$

In Equation (3), grad (f2(x, y)) is a differential value of the image signal, and k2 is a weighting parameter of approximately 0.3, for example.

In addition, as illustrated in item (VI) of FIG. 8, the threshold is finally determined by transferring the threshold to a surrounding region of 8 pixels, for example, transferring the threshold to the region by one pixel.

In addition, as illustrated in item (VII) of FIG. 8, since a pattern that is present on a die (edge die) located near the outer circumference of the wafer is inferior, a variation σ in the brightness of the corresponding local regions R is calculated in order to accept the inferiority to some extent and the threshold is corrected using the variation (standard deviation or the like) σ. Specifically, the threshold is corrected for the edge die on the basis of an edge factor (multiplication by σ ratio).

Figure 9:
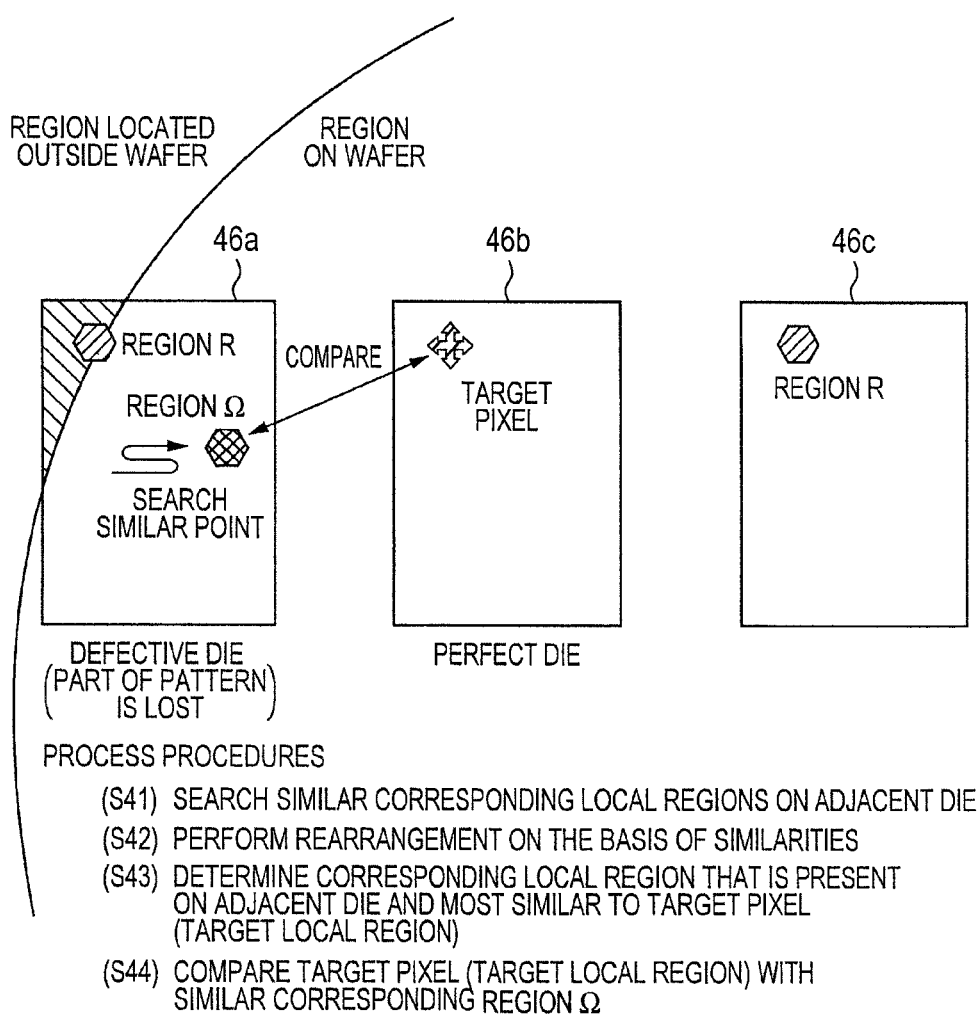
FIG. 9 is a diagram illustrating first process procedures performed on a wafer edge die (defective die) and a perfect die in a second embodiment of the signal processing unit included in the defect inspection device according to the present invention.

As described above, in the first embodiment of the signal processing unit 100 that is the feature of the present invention, the inspection is performed using the three dies (f1, f2, f3). This indicates that a circumferential portion (of the wafer) at which the number of dies is small can be reliably inspected. As a conventional example, there is a method described in Non-Patent Document 5 "Akira Hamamatsu, Hisae Shibuya, Hidetoshi Nishiyama, Yoshimasa Oshima, Shunji Maeda, Minori Nogushi "STATISTICAL THRESHOLD METHOD FOR SEMICONDUCTOR INSPECTION" View 2004 (2004)". In this method, it is necessary to acquire brightness information from a lot of dies in order to determine a threshold in a stable manner. In the first embodiment, the inspection can be performed with a high reliability even when the number of dies is small. As illustrated in FIG. 9, the edge die located near the circumferential portion of the wafer and a die located adjacent to the edge die can be inspected. Specifically, it is possible to inspect: a partial die on which a circuit pattern is not perfectly formed; and a die located adjacent to the partial die.

The following first process procedures are performed in a second embodiment of the signal processing unit 100 that is the feature of the present invention. In FIG. 9, (S41) similar corresponding local regions located on the adjacent dies are sequentially searched in images on a pixel basis, and a similarity is calculated for each of the similar corresponding local regions;

(S42) rearrangement is performed on the basis of the calculated similarities;

(S43) a corresponding local region that is present on any of the adjacent dies and most similar to the target pixel (target local region) is determined; and (S44) the target pixel (target local region) and the similar region Ω, which is a local region, are compared to each other.

The aforementioned comparison is performed through steps S34 to S38 of FIG. 3. The procedures can be changed.

Each of the similarities is the sum of absolute values of differences between pixels of the local regions, a square-root of the sum of squares of the differences, a correlation function, or the like. A concept called saliency can be used. The saliency is described in Non-Patent Document 6 "Tetsuya Asami, Takekazu Kato, Toshikazu Wada, Kaoru Sakai, Shunji Maeda "A saliency based abnormality detection algorithm for visual inspection" MIRU, IS5-2 (2008)". This method can be used. The aforementioned mutual information amounts can be used.

In the calculation of the similarities, positional displacement can be detected in the images. When the positional displacement is detected at a subpixel level using interpolation or the like, the sensitivity is improved.

When a similarity is lower than a set threshold, the comparison inspection cannot be performed and the interested pixel is output as an uninspected pixel. The threshold is set in advance. When the pixel is output as the uninspected pixel, the pixel is analyzed in detail later. For example, overlapping the inspection results in each dies and checking the frequencies of the uninspected pixels is performed.

Figure 10:
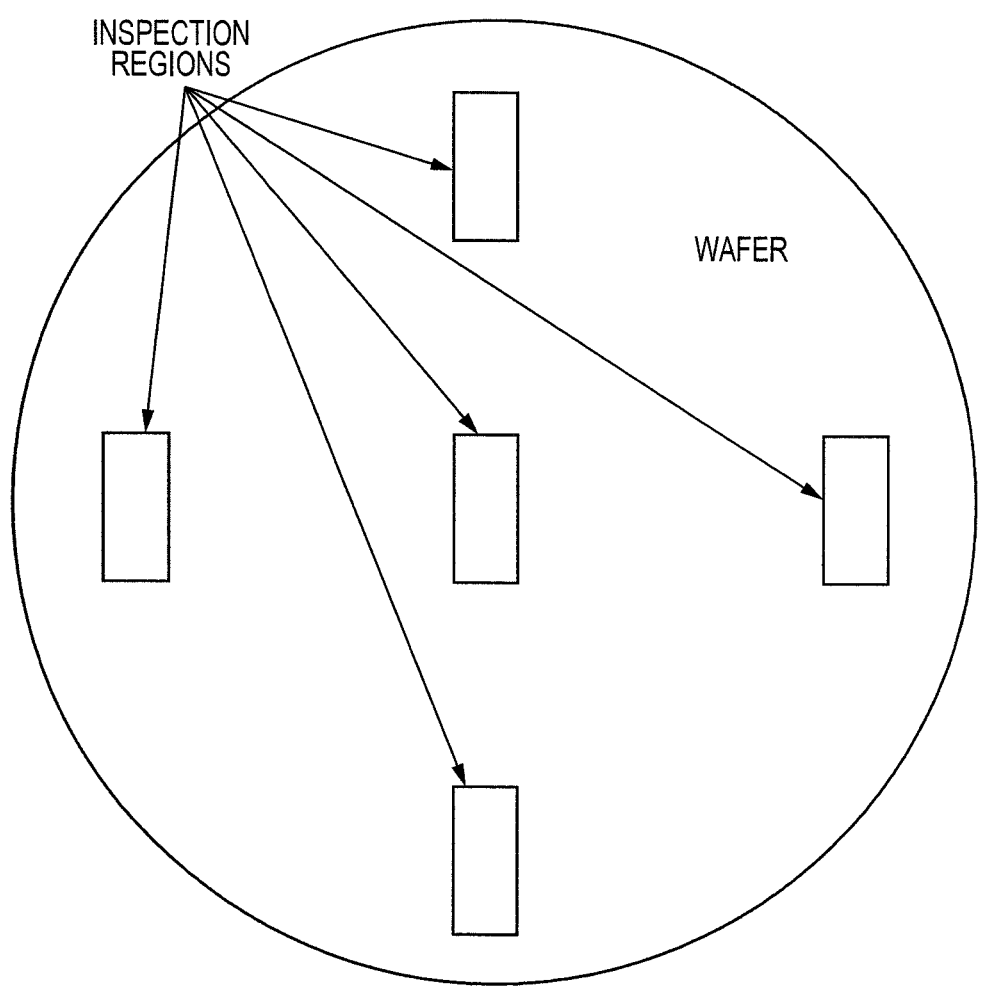
FIG. 10 is a diagram illustrating a limitation (to inspection regions) to be performed in the second embodiment of the signal processing unit included in the defect inspection device according to the present invention.

In addition, as illustrated in FIG. 10, even when a limited inspection of a part of the wafer needs to be performed, a lot of dies do not need to be inspected in the second embodiment. There is an advantage that the inspection can be achieved when only a region located around a die to be inspected is a target region. For example, the wafer can be inspected along a cross shape, or five points that are located on upper, lower and central portions of the surface of the wafer can be inspected. For example, in the aforementioned Non-Patent Document 6, a threshold is determined for a plurality of dies corresponding to one swath (images that are acquired by an image sensor while the stage is scanned in a single direction, and that are arranged in a single row in a lateral direction and cover both edges of the wafer). In order to inspect a part of the dies, it is necessary to acquire the images that are arranged in the single row in the lateral direction and cover both edges of the wafer. In the second embodiment, the inspection can be performed on the minimum number of dies even when a region to be inspected is limited, and the throughput is not reduced. In addition, a within-die limited inspection can be performed on a problem portion that is represented by a hot spot in which a margin for exposure or etching is insufficient. Specifically, information that is necessary to determine a threshold for a limited region is calculated from the minimum number of dies. Thus, it is not necessary that an image be unnecessarily detected and the stage be unnecessarily moved.

Next, second process procedures to be performed in the second embodiment of the signal processing unit 100 that is the feature of the present invention is described with reference to FIG. 11. The second process procedures to be performed in the second embodiment of the signal processing unit 100 are another example of the within-die comparison method and described as follows.
(S51) similar corresponding local regions located on the adjacent dies are searched;
(S52) rearrangement is performed on the basis of similarities;
(S53) corresponding local regions R1, R2, R3, . . . that are located on the adjacent dies and similar to the target region (target local region) are determined;
(S54) the target pixel (target local region) is compared with the corresponding local regions R1, R2, R3, . . . ; and
(S55) a defect is determined according to a multi-value logic such as a majority decision.

When the aforementioned second process procedures are performed and there are systematic defects (defects caused by an exposure device or the like) that are common to the dies, the defects can be inspected by the one-to-many comparison and the multi-value logic. The comparison with many dies is performed. Thus, even when roughness of a pattern exists, the inspection can be performed with high sensitivity. The multi-value logic may be a majority decision or a logical determination using a threshold.

In a conventional technique, a one-to-one comparison is performed, and the one-to-many comparison is not performed. Thus, it can be said that the one-to-many comparison is a new concept. The number of dies is limited, and a variation (in the dies) that is necessary for the comparison of the dies is accurately calculated. This eliminates unnecessary information. A lot of regions that are to be compared and are located in the adjacent dies are specified. A defect is comprehensively determined using adjacent regions that have similar features and is extracted with high sensitivity. The concept that is the one-to-many comparison is considered to be advanced since information that is necessary for the comparison is appropriately used.

The detailed logic of the one-to-many comparison is any of the following items.
(1) A binary logic in which a target region is determined as a defect when at least one portion does not match other corresponding portions or when the number of portions that do not match the other corresponding portions is equal to or larger than a threshold.
(2) A multi-value logic in which a target region is determined as a defect when differences are summed on the basis of differential images before the defect determination and the sum of the differences is equal to or larger than a threshold, or when the smallest value of the differences is detected and equal to or larger than a threshold, or when the largest value of the differences is detected and equal to or larger than a threshold. In this case, the differences may be weighted on the basis of similarities.
(3) A plurality of differential signals can be treated as multi-dimensional data. Specifically, the signals are treated as vectors, and the defect determination is performed on the basis of the lengths, orientations and the like of the vectors.

When steps S51 to S54 are performed before the inspection, the inspection throughput is not reduced. In addition, when adjacent dies that are located on the inner side of the wafer are used as the aforementioned adjacent dies, the inspection can be performed using the two adjacent dies at the most.

Figure 12:
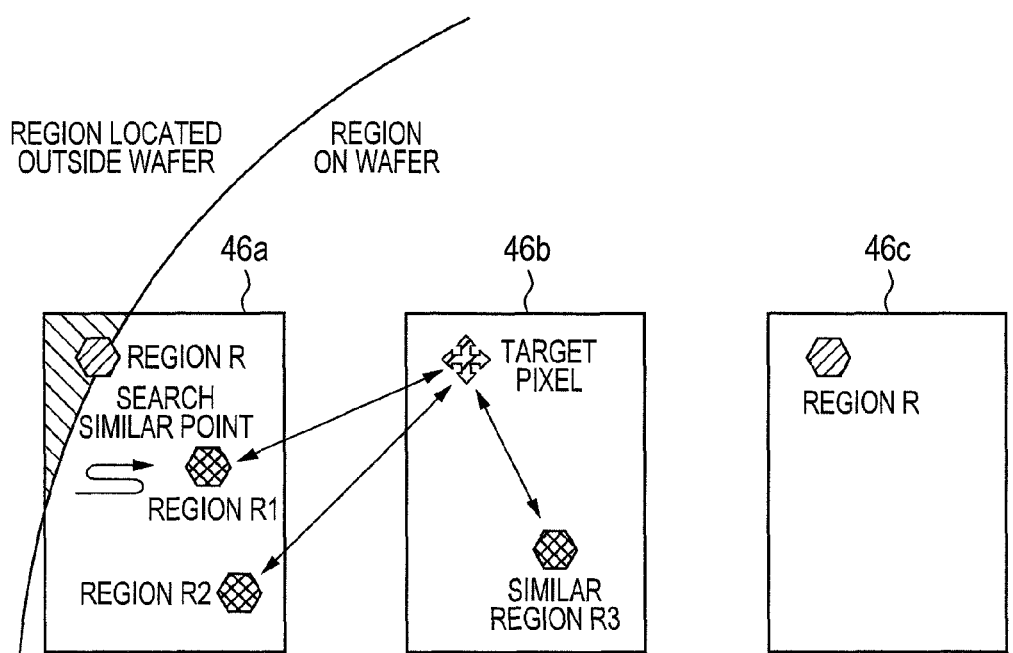
FIG. 12 is a diagram illustrating third process procedures of the within-die comparison method to be performed in the second embodiment of the signal processing unit included in the defect inspection device according to the present invention.

When regions that are included in the same die are compared in the aforementioned second process procedures, a variation in patterns is small and the inspection can be achieved with high sensitivity. FIG. 12 illustrates third process procedures. The third process procedures are performed by the signal processing unit 100 as follows.
(S61) Similar corresponding local regions that are located on the adjacent dies and the target die are searched;
(S62) rearrangement is performed on the basis of similarities;
(S63) the corresponding local regions R1, R2, R3, . . . that are located on the adjacent dies and the target die and similar to the target region (target local region) are determined;
(S64) the target region (target local region) is compared with the corresponding local regions R1, R2, R3, . . . ; and
(S65) a defect is determined according to a multi-value logic such as a majority decision.

The detailed logic of the one-to-many comparison is the same as the aforementioned comparison. In the comparison of local regions that are located on the target die, it is expected that the similarities of the local regions is high. Thus, when a weight is set, the weight that is set to the difference between the local regions is large.

In the first and second embodiments of the signal processing unit 100, the images that are obtained in the dark-field inspection illustrated in FIG. 1 are used. Since optical conditions (the wavelength of illumination, polarization of the illumination, an azimuth of the illumination, an elevation of the illumination, a numerical aperture for an illumination beam, an azimuth of light to be detected, an elevation of the light to be detected, polarization of the light to be detected, a numerical aperture for the light to be detected and the like) that enable a foreign material or any of various defects to be detected vary depending on the defect, it is necessary that the optical conditions be changed for each of the types of defects. However, even when the optical conditions are changed, the first and second embodiments can be applied without a problem.

Figure 13:
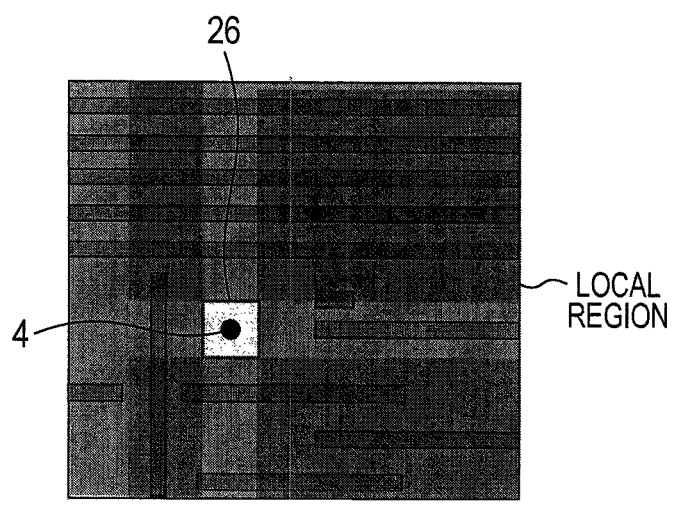
FIG. 13 is a diagram illustrating the case in which an aperture shape is set only in the vicinity of a defective portion in order to detect a distribution of light scattered only from a defect on an irregular pattern according to the present invention.

Next, an example of a method for optimizing each of the optical conditions is described. FIG. 13 is a plan view of the wafer. Reference numeral 4 indicates a defect to be detected. FIG. 13 illustrates the case in which the defect 4 is located in an aperiodic pattern region. In order to optimize an aperiodic spatial filter (not illustrated), it is necessary to detect a distribution of light scattered from the defect. A wide region is illuminated with the illumination light. Thus, in order to detect the distribution of the light scattered only from the defect 4, the shape 26 of an aperture needs to be set only around the defect by a field diaphragm (not illustrated) arranged in the detection optical system 20 as illustrated in FIG. 13. The size of the aperture is changed depending on the size of the defect and a positional relationship with a pattern located near the defect. For an LSI pattern, an appropriate length of each of sides of the aperture on the semiconductor wafer (substrate to be inspected) W is in a range of 1 mm to 10 mm (when the aperture is a circular aperture, the diameter of the aperture corresponds to the appropriate lengths). The field diaphragm that is arranged in the detection optical system causes a distribution of light scattered and detected by an observation camera (not illustrated) (that observes a Fourier transform image formed on the Fourier transform plane) to be a distribution of light scattered mainly from the defect. By setting the aperture of the aperiodic spatial filter at a location at which the luminescence of the scattered light is high, the light scattered from the defect can be detected while a detection of light scattered from a normal pattern is suppressed.

Figure 14:
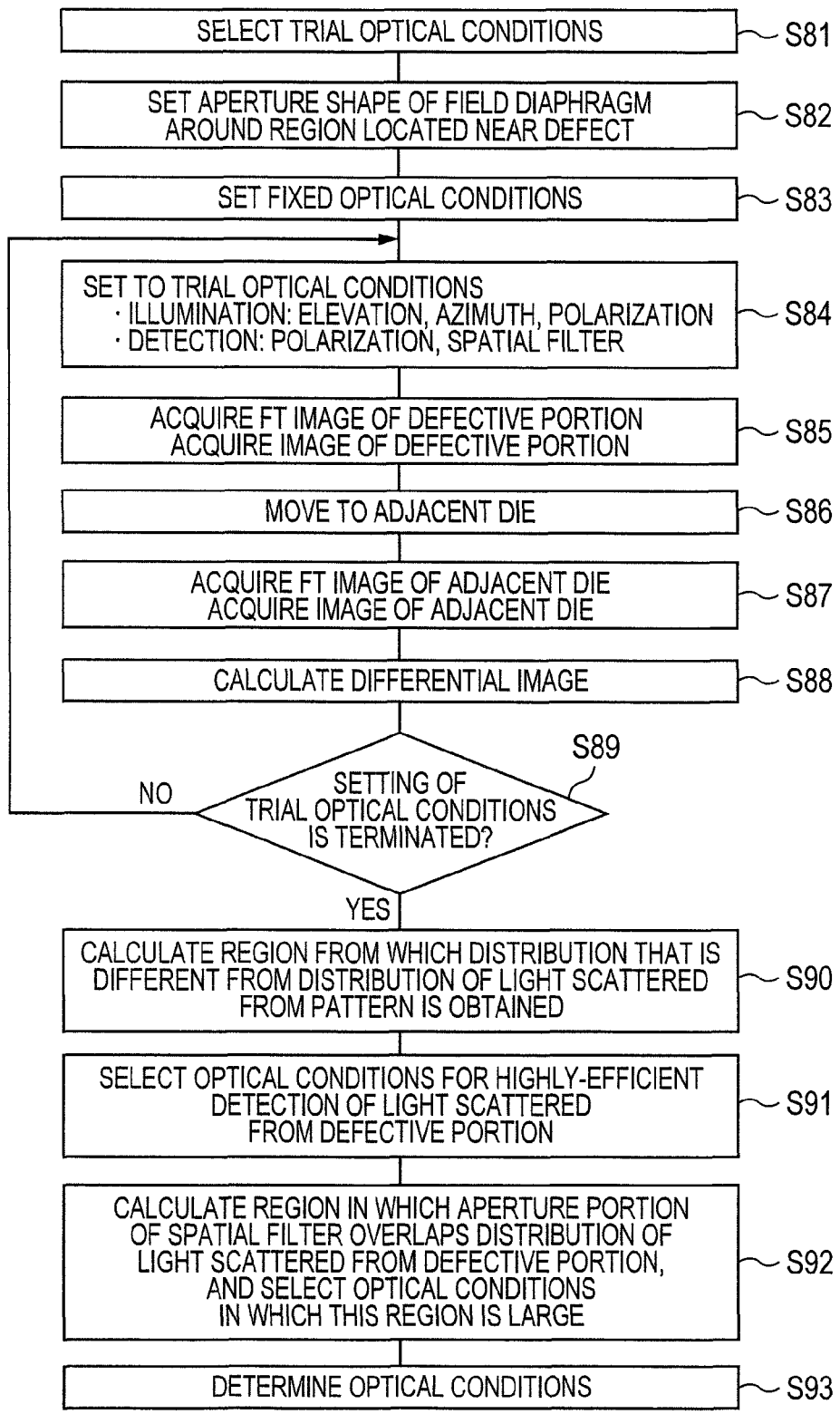
FIG. 14 is a flowchart of procedures of setting optical conditions in the defect inspection device according to the present invention.

Next, procedures of optimizing and setting optical conditions for a defect to be detected are described with reference to FIG. 14. Trial optical conditions that are to be first used are selected using a graphic user interface (GUI) of the whole controller 101 (S81). Next, the aperture shape of the field diaphragm included in the detection optical system 20 is set to pass the light scattered from the defect including around of it by using the GUI of the whole controller 101 on the basis of the screen illustrated in FIG. 13 (S82). Next, fixed optical conditions (a wavelength band of the illumination, the amount of the illumination, imaging magnification of the imaging lens 29 and the like) are set using the GUI (S83). Next, trial optical conditions are set using the GUI (S84).

As candidates for the trial conditions, the following items are provided, for example.
1. Illumination Optical System
(1-1) Elevation (angle between the surface of the wafer and a direction in which the illumination light propagates) of the illumination light 200
(1-2) Azimuth (for example, an angle between a direction in which the wafer is notched and the direction in which the illumination light propagates, or an angle between a direction in which the X-stage of the device moves and the direction in which the illumination light propagates) of the illumination light 200
(1-3) Polarization (P-polarization, S-polarization or the like) of the illumination light 200
(1-4) Numerical aperture for the illumination light 200
2. Detection Optical System (20)
(2-1) Rotational angle of the analyzer (not illustrated) that detects polarization of a specific component
(2-2) Shape of the aperture of the spatial filter and a birefringent material (the shape of the aperture and the birefringent material are selected after the aforementioned conditions are determined)

These conditions are optimized for each of defects by the following loop while being appropriately and temporarily set for each of the defects.

The following images are acquired: a dark-field image of a defective portion observed by a first observation camera (not illustrated) included in the detection optical system 20; and a Fourier transformed image of the defective portion observed by a second observation camera (not illustrated), and the images are stored in the image memory (S85). Next, the semiconductor wafer W is moved so as to the adjacent die comes into the viewing field of the first observation camera (S86). The following images are acquired from the adjacent die: a dark-field image of a normal portion observed by the first observation camera included in the detection optical system 20; and a Fourier transform image of the normal portion observed by the second observation camera, and the images are stored in the image memory of the signal processing unit 100 (S87). Then, the signal processing unit 100 calculates a differential image between the dark-field image and Fourier transform image of the defective portion and the dark-field image and Fourier transform image of the normal portion and stores the differential image in the image memory of the signal processing unit 100 (S88). The signal processing unit 100 or the whole controller 11 determines whether or not the setting of the trial optical conditions is terminated in step S89. When the setting of the trial optical conditions is not terminated, this process is repeated. The first and second observation cameras are configured so that optical paths can be switched to enable the dark-field images and the Fourier transform images to be observed for the setting of the optical conditions.

Next, the signal processing unit 100 or the whole controller 101 compares distributions of light scattered from the defective portion with distributions of light scattered from the normal portion on the basis of differential images between the dark-field images that represent the defective portion and are obtained under the variously set trial optical conditions and the dark-field images that represent the normal portion and are obtained under the variously set trial optical conditions; and the signal processing unit 100 or the whole controller 101 calculates optical conditions that cause a distribution of light scattered from the defective portion and a distribution of light scattered from the normal portion to be different, and outputs the calculated optical conditions using the GUI or the like (S90). In this case, the signal processing unit 100 or the whole controller 101 uses differential images between the Fourier transform images of the defective portion and the Fourier transform images of the normal portion, determines optical conditions that cause the distribution of light scattered from the defective portion and the distribution of light scattered from the normal portion to be different, and outputs the determined optical conditions using the GUI or the like. The scattered light distributions that are different from each other are caused by optical conditions that cause the intensity of the light scattered from the defective portion to be relatively higher than the light scattered from the normal portion or that cause light to be scattered from the defective portion and do not cause light to be scattered from the normal portion. Thus, the signal processing unit 100 or the whole controller 101 detects and selects optical conditions that enable a large amount of the light scattered from the defective portion to be efficiently detected (S91). The selected conditions may be multiple groups of conditions instead of a single group of the conditions.

In the procedures (S81 to S91) of setting optical conditions, optical conditions that enable a large amount of the light scattered from the defective portion to be detected can be found, and a position of the light scattered from the defective portion on the Fourier transform plane can be found. Next, a region that is located on the Fourier transform plane and in which the aperture portion of the spatial filter 28 overlaps the distribution of the light scattered from the defective portion is calculated, and optical conditions that cause the calculated region to be large are selected (S92).

Then, the signal processing unit 100 or the whole controller 101 terminates narrowing of optical conditions (S93). When multiple groups of optical conditions are selected by narrowing, a test inspection is performed under the narrowed optical conditions. Optical conditions that enable the defect and the normal pattern to be distinguished with high accuracy are selected on the basis of the results of the test inspection. Then, the setting of the optical conditions is terminated.

Various combinations of the configuration, functions and condition determination method described in the aforementioned example can be considered. In addition, in order to detect various defects at high speeds, it is necessary to simultaneously detect images under different groups of optical conditions. In this case, the setting of the optical conditions is performed in the procedures described above.

Figure 15:
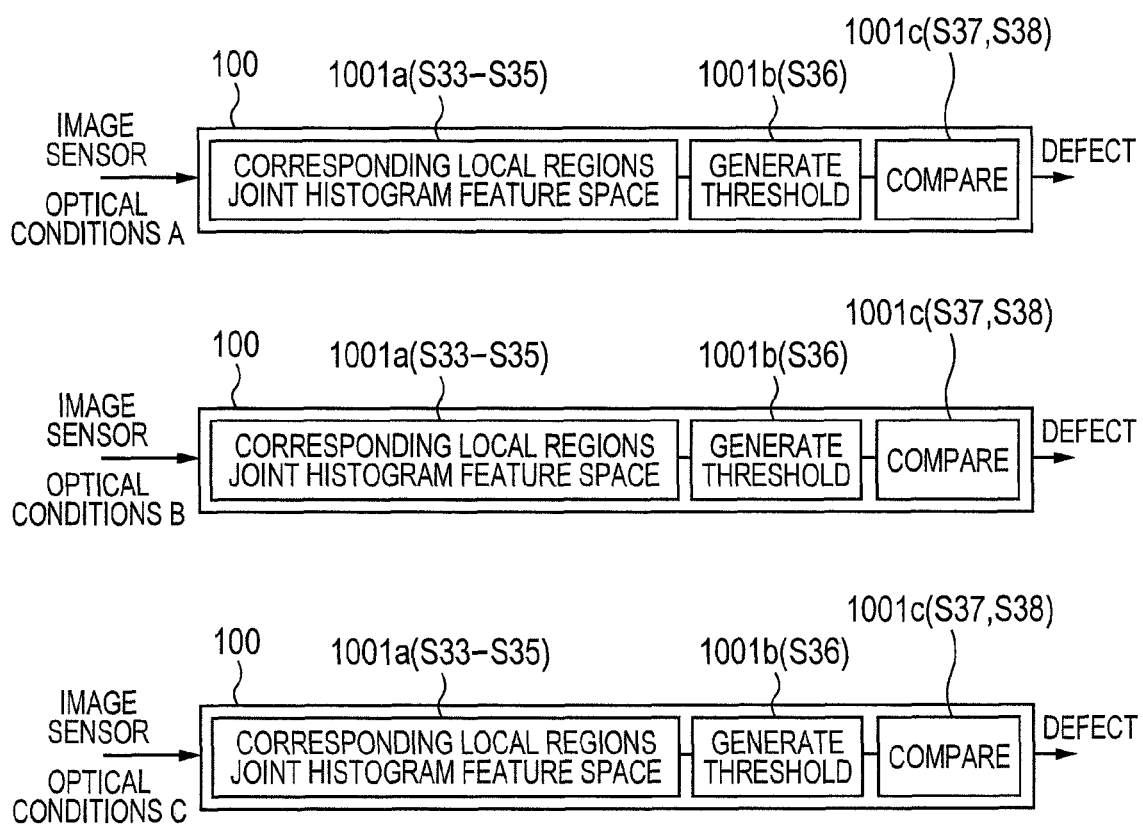
FIG. 15 is a diagram illustrating defect determination blocks that correspond to settings of a plurality of optical conditions according to the present invention.

In addition, when detecting images under plural optical conditions, the total amount of the images increases with an increase in the number of image sensors. In the present embodiment, as illustrated in FIG. 15, the pixels (to be compared) (the local regions R of the dies located adjacent to the target pixel illustrated in FIG. 5) that are used to form the joint histogram space (S33 to S35), generate the threshold (S36) and determine a defect through the comparison (S37, S38) are limited as much as possible. Thus, there is an advantage that processes are not large even in case of multiple groups A, B and C of optical conditions. Specifically, for the signal processing unit 100, a memory capacity that is necessary for configurations of blocks 1001a (S33 to S35), 1001b (S36) and 1001c (S37, S38) of image processing is small. The signal processing unit 100 can be achieved with low cost. Thus, there is an advantage that the signal processing unit is easily configured by a digital signal processor (DSP), a field programmable gate array (FPGA) or the like. Thus, it can be said that the present invention is applied to the simultaneous image detection and defect determination using multiple image sensors under multiple groups of optical conditions.

In FIG. 1, the illumination light 200 is a laser. However, a ramp may be used. The light that is emitted by an illumination light source may have a short wavelength or may be light (white light) having a wavelength in a wide wavelength band. When a wavelength band is appropriately selected, it can be expected that sensitivity of detecting a defect is improved. When the light having the short wavelength is used, light (ultraviolet light) that has a wavelength in an ultraviolet wavelength band can be used in order to increase a resolution of an image to be detected (or in order to detect a fine defect). When a laser is used as the light source and emits light with a single wavelength, means (not illustrated) for reducing coherence can be provided (to reduce temporal and spatial interference). As the image sensor 30, a time delay integration (TDI) image sensor that is constituted by a plurality of two-dimensionally arranged one-dimensional image sensors is used. The image sensor 30 is synchronized with a movement of the stage. A signal that is detected by each of the one-dimensional image sensors is transferred to a one-dimensional image sensor located at the next stage. The image sensor 30 sums the signals to obtain a high-sensitivity two-dimensional image. As the TDI image sensor, the parallel output type sensor that includes a plurality of output taps is used. Thus, data that is output from the sensor can be processed in parallel, and the detection can be performed at a high speed. A CMOS type linear sensor may be used. When the CMOS type linear sensor is used, a dynamic range can be increased.

In addition to images obtained by the dark-field inspection, the present invention can be applied to images that are obtained by a bright-field inspection. In the bright-field inspection, the illumination light source may be the laser or the ramp. In addition, the present invention can be applied to images obtained by an inspection using an electron beam. In each of those cases, the threshold can be determined on the basis of a small amount of data and the defect determination can be performed with high sensitivity without an adverse effect of the difference between the optical systems. In addition, even when systematic defects (defects caused by the exposure device or the like) that are common to the dies exist, the defects can be inspected by the one-to-many comparison and the multi-value logic. The comparison with many dies is performed. Thus, even when roughness of a pattern or the like exists, the inspection can be performed with high sensitivity.

As described above, in each of the inspection devices, selecting dies that are locating adjacent to the target die among dies formed on the wafer, and setting local regions in the selected dies for detecting light from the set local regions with the plural image sensors under the plural optical conditions. The brightness data of the local regions is extracted from the output of the plural image sensors. Then, information that is necessary and effective for the defect inspection is extracted from the extracted brightness data using the joint histogram feature space. The threshold for the defect determination is calculated on the basis of the extracted information, and the determination is performed through the comparison with high sensitivity. Thus, the aforementioned object can be accomplished.

The present invention can be applied to a mask, a reticle, FPD substrates for liquid crystal displays and plasma displays or the like in addition to the semiconductor wafer. The present invention can be applied to any substrate (such as a substrate provided with dies) that has a repeating pattern.

INDUSTRIAL APPLICABILITY

According to the present invention, the defect inspection device can be used as a device for inspecting a foreign material and a defect that occur during a process of manufacturing a semiconductor.

DESCRIPTION OF REFERENCE NUMERALS

4 . . . Defect, 20 . . . Detection optical system, 22 . . . Objective lens, 26 . . . Aperture shape, 28 . . . Spatial filter, 29 . . . Imaging lens, 30 . . . Linear sensor (one-dimensional image sensor), 31 . . . Pixel, 46a, 46b, 46c . . . Die (also called a chip), 53 . . . Pixel included in linear sensor and projected on wafer, 100 . . . Signal processing unit, 101 . . . Whole controller, 102 . . . External input/output system, 1031 . . . External display device, 103 . . . Peripheral device, 200 . . . Illumination light, 300 . . . Linear beam, 400 . . . Sensor output (image signal), 1000a . . . Corresponding local region/joint histogram feature space forming section, 1000b . . . Threshold generating section, 1000c . . . Local region comparing section, W . . . Wafer (substrate to be inspected)

The invention claimed is:

1. A defect inspection method for acquiring image signals from a substrate that is to be inspected, the substrate having circuit patterns repeatedly formed thereon, and inspecting a defect present on the substrate on the basis of the acquired image signals, the method comprising the steps of:

setting a target local region and a plurality of corresponding local regions in the acquired image signals, the target local region including a target pixel and an area surrounding the target pixel, and the corresponding local regions including pixels corresponding to the target pixel and areas surrounding the corresponding pixels;

searching for similarities between the image signal of the target local region set in the local region setting step and the image signals of the plurality of corresponding local regions set in the local region setting step;

determining, by using information of the similarities found in the searching step, a plurality of image signals that represent corresponding local regions and are similar to the image signal of the target local region;

comparing the image signal of the target local region with the image signals that represent the corresponding local regions and have been determined in the determining step;

determining a defect on the basis of differences found in the comparing of the image signal of the target local region with the image signals that represent the corresponding local regions;

forming a joint histogram feature space of the corresponding local regions on the basis of the image signals of the corresponding local regions set in the local region setting step;

determining a threshold on the basis of the joint histogram feature space formed in the forming step; and using the threshold determined in the threshold determining step to detect the defect present on the target local region on the basis of differential images between the target local region and the corresponding local regions.

2. A defect inspection device for acquiring image signals from a substrate that is to be inspected and has circuit patterns repeatedly formed and inspecting a defect present on the substrate on the basis of the acquired image signals, the defect inspection device comprising:

local region setting unit configured to set a target local region and a plurality of corresponding local regions in the acquired image signals, the target local region including a target pixel and an area surrounding the target pixel, and the corresponding local regions including pixels corresponding to the target pixel and areas surrounding the corresponding pixels;

searching unit configured to search for similarities between the image signal of the target local region set by the local region setting unit and the image signals of the plurality of corresponding local regions set by the local region setting unit;

determining unit configured to determine, by using information of the similarities found by the searching unit, a plurality of image signals that represent corresponding local regions and are similar to the image signal of the target local region;

defect determining unit configured to compare the image signal of the target local region with the image signals that represent the corresponding local regions and have been determined by the defect determining unit, and to determine a defect on the basis of differences found in the comparison of the image signal of the target local region with the image signals that represent the corresponding local regions;

forming unit configured to form a joint histogram feature space of the corresponding local regions on the basis of the image signals of the corresponding local regions set by the local region setting unit;

threshold determining unit configured to determine a threshold on the basis of the joint histogram feature space formed by the forming unit; and defect detecting unit configured to use the threshold determined by the threshold determining unit to detect the defect present on the target local region on the basis of differential images between the target local region and the corresponding local regions.

3. A defect inspection method for acquiring image signals from a substrate that is to be inspected, the substrate having circuit patterns repeatedly formed thereon, and inspecting a defect present on the substrate on the basis of the acquired image signals, the method comprising the steps of:

setting a target local region and a plurality of corresponding local regions in the acquired image signals, the target local region including a target pixel and an area surrounding the target pixel, and the corresponding local regions including pixels corresponding to the target pixel and areas surrounding the corresponding pixels;

forming a joint histogram feature space of the corresponding local regions on the basis of the image signals of the corresponding local regions set in the local region setting step;

determining a threshold on the basis of the joint histogram feature space formed in the forming step; and detecting the defect present on the target local region on the basis of differential images between the target local region and the corresponding local regions by using the threshold determined in the threshold determining step.

4. The defect inspection method according to claim 3, wherein in the forming step, the joint histogram feature space of the corresponding local regions is formed with axes that indicate brightness and a difference, which are calculated from the image signals of the corresponding local regions.

5. The defect inspection method according to claim 4, wherein in the threshold determining step, a convex hull is calculated from the joint histogram feature space of the corresponding local regions, and the threshold is determined on the basis of the convex hull, the joint histogram feature space being formed in the forming step.

6. The defect inspection method according to claim 4, wherein in the threshold determining step, the maximum value (Diff) of differences, and brightness (Bs) corresponding to the maximum value of the differences, are calculated from the joint histogram feature space of the corresponding local regions, and the threshold is determined by using the calculated maximum value (Diff) of the differences and the brightness corresponding to the maximum value (Diff) on the basis of brightness (Bf) obtained from the image signal of the target local region set in the local region setting step, the joint histogram feature space being formed in the forming step.

7. The defect inspection method according to claim 3, further comprising:

an image improving step of using a point spread function indicating a degradation of an optical system to restore degradations of the image signals acquired from the substrate to be inspected before the local region setting step.

8. A defect inspection device for acquiring image signals from a substrate that is to be inspected, the substrate having circuit patterns repeatedly formed thereon, and inspecting a defect present on the substrate on the basis of the acquired image signals, the defect inspection device comprising:

local region setting unit configured to set a target local region and a plurality of corresponding local regions in the acquired image signals, the target local region including a target pixel and an area surrounding the target pixel, and the corresponding local regions including pixels corresponding to the target pixel and areas surrounding the corresponding pixels;

forming unit configured to form a joint histogram feature space of the corresponding local regions on the basis of the image signals of the corresponding local regions set by the local region setting unit;

threshold determining unit configured to determine a threshold on the basis of the joint histogram feature space formed by the forming unit; and defect detecting unit configured to detect the defect present on the target local region on the basis of differential images between the target local region and the corresponding local regions by using the threshold determined by the threshold determining unit.

9. The defect inspection device according to claim 8, wherein the forming unit is configured to form the joint histogram feature space of the corresponding local regions, while axes of the joint histogram feature space indicate brightness and a difference, which are calculated from the image signals of the corresponding local regions.

10. The defect inspection device according to claim 9, wherein the threshold determining unit is configured to calculate a convex hull from the joint histogram feature space of the corresponding local regions, and to determine the threshold on the basis of the convex hull, the joint histogram feature space being formed by the forming unit.

11. The defect inspection device according to claim 9, wherein the threshold determining unit is configured to calculate the maximum value (Diff) of differences and brightness (Bs) corresponding to the maximum value of the differences from the joint histogram feature space of the corresponding local regions, and to determine the threshold by using the calculated maximum value (Diff) of the differences and the brightness corresponding to the maximum value (Diff) on the basis of brightness (Bf) obtained from the image signal of the target local region set by the local region setting unit.

12. The defect inspection device according to claim 8, further comprising: an image improving unit configured to use a point spread function indicating a degradation of an optical system to restore degradations of the image signals acquired from the substrate to be inspected.

\* \* \* \* \*